US00PP21709P2

(12) United States Plant Patent
Carruth

(10) Patent No.: US PP21,709 P2
(45) Date of Patent: Feb. 15, 2011

(54) FLORIBUNDA ROSE PLANT NAMED 'WEKCOBEJU'

(50) Latin Name: *Rosa hybrida*
Varietal Denomination: WEKcobeju

(75) Inventor: Thomas F. Carruth, Altadena, CA (US)

(73) Assignee: Weeks Wholesale Rose Grower, Inc., Pomona, CA (US)

( * ) Notice: Subject to any disclaimer, the term of this patent is extended or adjusted under 35 U.S.C. 154(b) by 0 days.

(21) Appl. No.: 12/590,206

(22) Filed: Nov. 4, 2009

(51) Int. Cl.
*A01H 5/00* (2006.01)

(52) U.S. Cl. ..... Plt./141
(58) Field of Classification Search ..... Plt./141
See application file for complete search history.

(56) References Cited

U.S. PATENT DOCUMENTS

PP18,473 P2 2/2008 Carruth
PP18,870 P2 6/2008 Carruth

*Primary Examiner*—Annette H Para
(74) *Attorney, Agent, or Firm*—McKee, Voorhees & Sease, P.L.C.

(57) ABSTRACT

A new variety of Floribunda rose suitable for garden decoration, having flowers of smoky lavender and rusty red-orange coloration.

1 Drawing Sheet

Classification: The present invention relates to a new *Rosa hybrida* plant.

Variety denomination: The new plant has the varietal denomination 'WEKcobeju'.

BACKGROUND OF THE INVENTION

This invention relates to a new and distinct variety of Floribunda Rose. It has as its seed parent the variety known as 'WEKcocbeb' (U.S. Plant Pat. No. 18,870) and as its pollen parent the variety known as 'WEKvossutono' (U.S. Plant Pat. No. 18,473).

SUMMARY OF THE INVENTION

Among the features which distinguish the new variety from other presently available and commercial rose cultivars known to the inventor are the following combinations of characteristics: its unique flowers of smoky lavender and rusty red-orange coloration, its mucronate outer and intermediate petals apices and its heavy purple suffusion on the petals as they age. The plant has a bushy rounded growing habit, suitable for outdoor garden decoration.

Asexual reproduction of the new variety by budding as performed in Kern County and Pomona, Calif., shows that the foregoing and other distinguishing characteristics come true to form and are established and transmitted through succeeding asexual propagations. 'WEKcobeju' may be asexually propagated by cuttings, budding and grafting. The budding and grafting successfully occurred on the plant/rootstock *Rosa hybrida* cv. 'Dr. Huey' (not patented).

COMPARISON WITH PARENTS

The new rose may be distinguished from its seed parent, 'WEKcocbeb' by the following combination of characteristics: whereas 'WEKcobeju' bears flowers of smoky lavender and rusty red-orange coloration with double petalage (about 16 to 24 petals), 'WEKcocbeb' bears flowers of brilliant scarlet coloration with a white reverse and with significantly lesser petalage (about 10 to 17 petals). The new variety has a bushy rounded growing habit (about 120 to about 160 cm. in height), whereas the seed parent has a bushy moderately spreading significantly shorter growing habit (about 80 to about 100 cm. in height).

The new variety may be distinguished from its pollen parent, 'WEKvossutono' by the following combination of characteristics: whereas 'WEKcobeju' bears flowers of smoky lavender and rusty red-orange coloration with double petalage (about 16 to 24 petals), 'WEKvossutono' bears butter gold flowers with significantly heavier petalage (about 30 to 45 petals). The new variety has a bushy rounded growing habit (about 120 to about 160 cm. in height), whereas the pollen parent has a compact and bushy significantly shorter growing habit (about 70 to about 85 cm. in height).

COMPARISON WITH THE CLOSEST COMMERCIALLY AVAILABLE CULTIVAR

The new variety has very unique characteristics that distinguish it from any other commercially available cultivar. No variety can compare to 'WEKcobeju'.

BRIEF DESCRIPTION OF ILLUSTRATION

The accompanying photograph illustrates the new variety and shows the flowering thereof from bud to full bloom depicted in color as nearly correct as it is possible to make in a color illustration of the character. Throughout this specification, color references and/or values are based upon the Colour Chart of The Royal Horticultural Society (1966) except where common terms of color definition are employed.

DESCRIPTION OF THE NEW VARIETY

The following description is of 3 to 4 year-old rose plants of the new variety grown outdoors in Pomona, Calif. in the month of October. Phenotypic expression may vary with environmental, cultural and climatic conditions, as well as differences in conditions of light and soil.

FLOWER

The new variety usually bears its flowers in clusters of two to eleven or more per stem. Flowers are borne in regular rounded clusters on strong medium length stems (about 18 to about 44 cm.). Outdoors, the plant blooms abundantly and nearly continuously during the growing season. The flowers have a slight apple-like to somewhat pear-like fragrance.

BUD

The peduncle is about 1.6 to about 4.2 cm. in length, of slender caliper (about 0.1 cm to about 0.2 cm. in diameter), and usually erect. It is moderately smooth, with some stipitate glands. Peduncle color is between 146B and 146A sometimes lightly suffused, especially on the side exposed to the sun, with between 183B and 187B.

Before the calyx breaks, the bud is about 0.9 to about 1.6 cm. in diameter at the widest point, about 1.4 to about 1.9 cm. in length, and pointed in shape. The surface of the bud bears few foliaceous appendages and some stipitate glands, usually with slender entire foliaceous parts extending beyond the tip of the bud about ½ or more of its length. Bud color is between 146B and 146A sometimes lightly suffused, especially on the side exposed to the sun, with between 183B and 187B.

The sepals are about 2.2 to about 3.3 cm. in length and about 0.6 to about 1.0 cm. in width at the widest point. The outer surface color of the sepal is between 146B and 146A sometimes lightly suffused, especially on the side exposed to the sun, with between 183B and 187B. The inner surface color of the sepal is near 138B broadly bordered by near 137A. After the sepals open, the inner surface color is sometimes lightly suffused, especially on the area exposed to the sun, with between 187A and 187B. The inner surface of the sepal is covered with fine wooly tomentum; sepal margins are lined with few stipitate glands and many hairs.

The receptacle of the flower is of medium length (about 0.3 to about 0.6 cm.) and average in caliper (about 0.6 to about 0.8 cm. in diameter). The receptacle is cup-shaped in form. Its surface is smooth with few hairs and stipitate glands and with thick fleshy walls. The receptacle color is between 146B and 146A.

As the petals open (after the calyx breaks), the bud is about 1.4 to about 2.4 cm. in diameter at the widest point, about 2.1 to about 3.1 cm. in length, and moderately ovoid to somewhat pointed in form. The color at the base of the under surfaces of the newly opened petals is between 53B and 60B gradually suffusing toward the edge of the petals with between 53A and 60A. At the point where the petal attaches, there is a moderately large zone of between 13B and 12A. The color at the base of the upper surfaces of the newly opened petals is between 46B and 45B often heavily blushed especially on the upper ⅓ of the petal with between 187A and 60A. At the point where the petal attaches, there is a moderately large zone of between 13B and 12A.

BLOOM

When fully open, the bloom ranges from about 6.3 to about 10.1 cm. in diameter. Petalage is double with about 16 to 24 petals and about 7 to 12 petaloids irregularly arranged. When partially open, the bloom form is moderately cupped to somewhat high centered, and the petals are loosely spiraled to cupped with petal edges somewhat reflexed outward. When fully open, the bloom form is more cupped to somewhat flat, and the petals are loosely cupped to moderately undulated with petal edges moderately reflexed outward and sometimes somewhat reflexed inward.

PETALS

The substance of the petals is somewhat slight and of moderately thin thickness, with upper surfaces moderately satiny and under surfaces slightly shiny to matte. The petals are about 2.1 to about 4.1 cm. in length and about 1.2 to about 3.4 cm. in width at the widest point. Petal margins are entire.

The outer petals are moderately obovate in shape with mucronate apices.

The inner petals are moderately obovate to somewhat oblanceolate in shape with rounded apices.

Petaloids are about 0.6 to about 1.9 cm. in length and about 0.3 to about 1.4 cm. in width at the widest point. Petaloids are irregularly shaped somewhat oblanceolate to subulate with rounded apices.

NEWLY OPENED FLOWER

The under surface color of the outer, intermediate and inner petals is between 53C and 184D. At the point where the petal attaches, there is a moderately large zone of between 13C and 12B. The upper surface color of the outer, intermediate and inner petals is between 44C and 45C usually lightly overlaid with a wash of between 77A and 79C. At the point where the petal attaches, there is a moderately large zone of between 13C and 12B.

The under and upper surface colors of the petaloids are similar in coloration to the upper and under surfaces of the intermediate and inner petals.

The general tonality of the newly opened flower is between 44C and 45C usually lightly overlaid with a wash of between 77A and 79C.

THREE-DAY-OLD FLOWER

The under surface color of the outer, intermediate and inner petals is between 53C and 185C. At the point where the petal attaches, there is a moderately large zone of between 11B and 10B. The upper surface color of the outer, intermediate and inner petals is between 47C and 44D usually lightly overlaid with a wash of between 77A and 79C. At the point where the petal attaches, there is a moderately large zone of between 8B and 7D.

The under and upper surface colors of the petaloids are similar in coloration to the upper and under surfaces of the intermediate and inner petals.

The general tonality of the three-day-old flower is between 47C and 44D usually lightly overlaid with a wash of between 77A and 79C.

On the spent bloom, the petals usually drop off cleanly, aging to between 60C and 186A on the under surface and to between 48B and 51B on the upper surface usually heavily overlaid with a wash of between 79D and 79C.

In October in Pomona, Calif., blooms on the bush growing outdoors generally last about four to five days. Cut roses from plants grown outdoors and kept at normal indoor living temperatures generally last about four to five days.

MALE REPRODUCTIVE ORGANS

Stamens are average in number (average about 75) and are arranged regularly about the pistils; a few are mixed with petaloids. The filaments are of variable length (about 0.3 to about 0.9 cm.) most with anthers. Filaments are between 13A and 14B in color. The anthers are moderately small for the class and all open approximately at the same time. Anther color when immature is near 23B on the external part and near 9D on the internal part. Anther color at maturity is near 164C on the external part and near 200A on the internal part. Pollen is abundant and between 16D and 18B in color.

FEMALE REPRODUCTIVE ORGANS

Pistils vary in number (average about 55). The styles are moderately even, somewhat long in length (about 0.7 to about 0.9 cm.), average in caliper, and loosely bunched to somewhat separated. Stigma color is near 6C. Style color is between 154C and 150C often heavily suffused with near 53B. Ovaries are usually all enclosed in the calyx.

Hips are of moderately short length (about 1.2 to about 1.7 cm.), rounded to somewhat globular in form, and between 28A and 30C in color when ripe. The hip surface is very smooth with thick fleshy walls. The sepals are fugacious, and usually straight in shape.

The seeds are irregularly rounded, smooth in texture, approximately 2 to about 7 per hip, about 0.5 to about 0.7 cm. in diameter at the widest point and between 164B and 165C in color.

FOLIAGE

The compound leaves are usually comprised of three to seven leaflets and are borne abundantly. The seven-leaflet leaves are about 9.2 to about 15.8 cm. in length and about 6.9 to about 11.4 cm. in width at the widest point, moderately leathery to somewhat crisp in texture, and glossy in finish on the upper side and matte in finish on the under side. The terminal leaflets are about 4.9 to about 6.6 cm. in length and about 2.4 to about 4.1 cm. in width at the widest point, shaped oval to somewhat lanceolate with acute apices and rounded to moderately acute bases. Their margins are usually simply serrate.

The upper surface color of the mature leaf is between 137A and 146A. The under surface color of the mature leaf is between 147B and 146B. The upper surface color of the young leaf is between 137B and 146A, often heavily suffused with between 187A and 183A. The under surface color of the young leaf is between 146A and 146B, often heavily suffused with between 187B and 183A.

The rachis is average in caliper and rough. The upper side is shallowly grooved with few hairs and stipitate glands on the edges of the grooves. The under side of the rachis is rough with some stipitate glands and small prickles. The rachis color is near 145B on the under side and near 146A on the upper side often heavily suffused on the young leaf with between 187B and 183A.

The stipules are about 0.9 to about 2.1 cm. in length and moderately wide (about 0.5 to about 0.8 cm.) with medium length straight points that usually turn out at an angle of more than 45 degrees and sometimes recurve toward the stem. The stipule color is between 137B and 137C often heavily suffused on the young leaf with between 187B and 187A.

The petiole is average in caliper and rough. The upper side is shallowly grooved with few hairs and stipitate glands on the edges of the grooves. The under side of the petiole is rough with some stipitate glands and small prickles. The petiole is about 0.6 to about 2.0 cm. in length and about 0.1 to about 0.2 cm in diameter at the widest point. The petiole color is near 145B on the under side and near 146A on the upper side often heavily suffused on the young leaf with between 187B and 183A.

The plant displays an above average degree of resistance to powdery mildew and rust as compared to other commercial varieties grown under comparable conditions in Pomona, Calif. The plant's winter hardiness and drought/heat tolerance are yet to be determined.

GROWTH

The plant has a bushy rounded medium height growing habit (about 120 to about 160 cm. in height and about 120 to about 160 cm. spread at the widest point), with very full branching. It displays vigorous growth and the canes are of medium caliper for the class (about 1.1 to about 1.9 cm. in width at the widest point).

The color of the major stems is between 147B and 146A. They bear many large prickles that are about 0.6 to about 0.8 cm. in length. The large prickles are angled moderately downward with a medium length somewhat broad oval base; prickle color is between 165A and 177A. The major stem bears many small prickles of similar shape and coloration.

The color of the branches is between 146B and 146A. They bear many large prickles which are of similar size and shape to the large prickles on the major stems; prickle color is near 161A often moderately suffused with between 187C and 187D. The branches bear few small prickles of similar shape and coloration.

The color of the new shoots is between 146B and 146A often heavily suffused with between 187B and 183A. They bear many large prickles which are of similar size and shape to the large prickles on the major stems; prickle color is between 152D and 153A often heavily suffused with between 187A and 187B. The shoots bear few small prickles of similar shape and coloration.

I claim:

1. A new and distinct Floribunda rose plant of the variety substantially as described and illustrated herein.

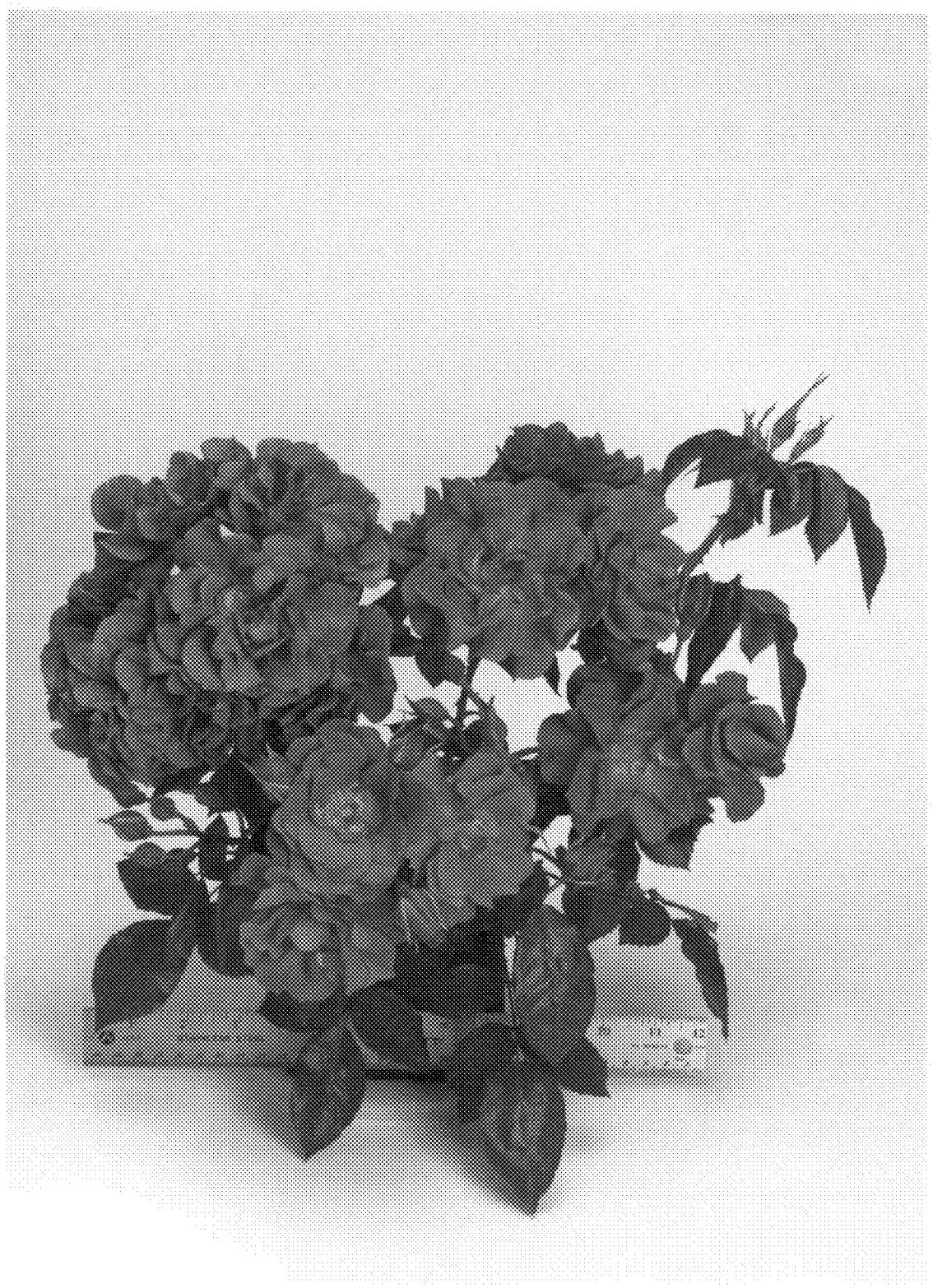

* * * * *